(12) United States Patent
Kamiyama

(10) Patent No.: US 6,991,606 B2
(45) Date of Patent: Jan. 31, 2006

(54) ULTRASONIC DIAGNOSIS APPARATUS AND CONTROL METHOD OF ULTRASONIC DIAGNOSIS APPARATUS

(75) Inventor: Naohisa Kamiyama, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/603,806

(22) Filed: Jun. 26, 2003

(65) Prior Publication Data

US 2004/0010194 A1 Jan. 15, 2004

Related U.S. Application Data

(63) Continuation of application No. PCT/JP01/11385, filed on Dec. 25, 2001.

(30) Foreign Application Priority Data

Dec. 26, 2000 (JP) .................................... 2000-395721

(51) Int. Cl.
*A61B 8/14* (2006.01)

(52) U.S. Cl. .................................................. 600/458
(58) Field of Classification Search ......... 600/437–472; 424/9.51–9.53; 73/625, 626; 128/916
See application file for complete search history.

(56) References Cited

U.S. PATENT DOCUMENTS

| | | | |
|---|---|---|---|
| 5,694,937 A | 12/1997 | Kamiyama | |
| 5,833,613 A | 11/1998 | Averkiou et al. | |
| 5,860,931 A | * 1/1999 | Chandler | 600/458 |
| 5,944,666 A | * 8/1999 | Hossack et al. | 600/458 |
| 6,224,554 B1 | * 5/2001 | Tickner et al. | 600/438 |
| 6,561,982 B2 | * 5/2003 | Greppi et al. | 600/458 |

FOREIGN PATENT DOCUMENTS

| | | |
|---|---|---|
| JP | HEI 8-182680 A | 7/1996 |
| JP | HEI 8-280674 A | 10/1996 |
| JP | HEI 10-75951 A | 3/1998 |
| JP | HEI 11-137550 A | 5/1999 |
| JP | 11-137550 | 5/1999 |
| JP | HEI 11-253449 A | 9/1999 |
| JP | 11-253449 | 9/1999 |
| WO | WO 00/57792 | 10/2000 |

OTHER PUBLICATIONS

Naohisa Kamiyama et al., "Flash Echo Eizou–hou no Kentou (5); negative pressure threshold ni tsuite", Chouonpa Igaku, Mar. 15, 1997, vol. 24, No. 3, p. 326.

* cited by examiner

*Primary Examiner*—Ali Imam
(74) *Attorney, Agent, or Firm*—Oblon, Spivak, McClelland, Maier & Neustadt, P.C.

(57) ABSTRACT

In transmissions of each frame through intermittent transmissions, by performing ultrasonic wave transmissions while increasing a mechanical function step by step, destructions of bubbles of a contrast medium can be induced step by step according to their different sizes. By generating ultrasonic images using the destructions at the respective steps as the sources of echoes, it is possible to provide new ecological information including, for example, information reflecting the dynamics of substances smaller than the red blood cells, the distribution of predatory cells, new diagnosis information, etc.

18 Claims, 6 Drawing Sheets

ULTRASONIC DIAGNOSIS APPARATUS AND CONTROL METHOD OF ULTRASONIC DIAGNOSIS APPARATUS

CROSS-REFERENCE TO RELATED APPLICATIONS

This is a Continuation Application of PCT Application No. PCT/JP01/11385, filed Dec. 25, 2001, which was not published under PCT Article 21(2) in English.

This application is based upon and claims the benefit of priority from the prior Japanese Patent Application No. 2000-395721, filed Dec. 26, 2000, the entire contents of which are incorporated herein by reference.

BACKGROUND OF THE INVENTION

1. Field of the Invention

The present invention relates to an ultrasonic diagnosis apparatus adaptable to contrast echo imaging diagnosis, and a control method thereof.

2. Description of the Related Art

An ultrasonic imaging diagnosis apparatus displays a tomographic image of tissue through a non-invasive examination method using an ultrasonic wave. The ultrasonic imaging diagnosis apparatus is quite useful at clinics, for example, beat pulsation of the heart or motion of a fetus can be displayed in real time through a manipulation as simple as placing an ultrasonic probe to the body surface, a screening can be performed repetitively owing to its high safety, and it can be moved to a bedside for a screening to be conducted owing to its small system size in comparison with other diagnosis equipment for X-ray imaging, CT imaging, MRI, etc. In addition, although an ultrasonic diagnosis apparatus differs extensively depending on the types, there has been recently developed an ultrasonic diagnosis apparatus so small in size that one can carry it around with one hand. There is a possibility that an ultrasonic diagnosis apparatus the patient can manipulate by himself will be developed in the near future.

Incidentally, with the recent commercialization of ultrasonic contrast media of an intravenous infusion type, an ultrasonic diagnosis through the contrast echo imaging method has been becoming popular. The contrast echo imaging method is aimed at evaluating the dynamics of a blood flow, for example, in a screening of the heart, the abdominal organs and the like, by introducing an ultrasonic contrast medium into a vein and thereby enhancing a blood flow signal. Many of contrast media use micro-bubbles as sources of reflections, and the higher the quantity and concentration of the introduced contrast medium become, the higher the effect of contrast imaging becomes. On the other hand, it has been known that bubbles, being a delicate base material by nature, collapse upon irradiation of ultrasonic waves, which shortens an effective time for contrast imaging.

In general, a blood flow often means red blood cells. Ideally speaking, it is preferable that a contrast medium used for an ultrasonic diagnosis shows the same dynamics as those of the red blood cells. In practice, however, the contrast medium is now known to have dynamics different from those of the red blood cells.

For example, many of ultrasonic contrast media are known to cause retention in the parenchyma of the liver, and it is thought that foreign-body uptake cells in the sinusoid of the liver ingest the retained contrast medium (needless to say, the red blood cells are not ingested). Also, blood capillaries within the body include cavities of a size that allows a liquid component (blood plasma) to seep out, so that cells are supplied with nutrition or oxygen. Although the cavities of the blood capillaries are too small of a size for the red blood cells to pass through, it is predicted that some of contrast media leak to the outside through the cavities in the blood capillary wall depending on the bubble size (the average diameter of the red blood cells is approximately 8 $\mu$m, and it is thought that the bubbles of a contrast medium having a size of approximately 8 $\mu$m at the maximum and 0.5 $\mu$m or less at the minimum are circulating throughout the body).

However, it remains unclear whether the contrast medium constantly reflects the dynamics of circulating blood, and for example, in a case where bubbles are retained in a micro circulation system, ecological information using the destruction of bubbles as the sources of echoes may not reflect the dynamics of circulating blood. In such a case, it may become difficult to observe the true dynamics of the red blood cells even when enhancement in intensity by a contrast medium is achieved.

The invention was devised in view of the foregoing situations, and therefore provides an ultrasonic diagnosis apparatus capable of observing or quantifying bubbles of a contrast medium of a size comparable to the red blood cells and bubbles of the contrast medium of a sufficiently smaller size independently through control of a degree of disappearance of the bubbles by changing transmission conditions.

BRIEF SUMMARY OF THE INVENTION

In order to achieve the above object, the invention provides means as follows.

That is, the invention provides an ultrasonic diagnosis apparatus for acquiring an ultrasonic tomographic image by scanning a diagnostic target within a subject to be diagnosed with an ultrasonic wave, which apparatus is characterized by being provided with irradiation means for irradiating, to a specific tomographic layer of the subject to be diagnosed, a first ultrasonic wave used to destroy bubbles of a contrast medium present in blood in a blood vessel and tissue fluid and lymph outside the blood vessel within the subject to be diagnosed, and a second ultrasonic wave used to destroy remaining bubbles of the contrast medium that were not destroyed by the first ultrasonic wave and are flowing in blood in the blood vessel within the subject to be diagnosed.

According to this arrangement, it is possible to achieve an ultrasonic diagnosis apparatus capable of observing or quantifying bubbles of a contrast medium of a size comparable to the red blood cells and bubbles of the contrast medium of a sufficiently smaller size independently through control of a degree of disappearance of bubbles by changing transmission conditions.

DETAILED DESCRIPTION OF THE INVENTION

Figure 1:
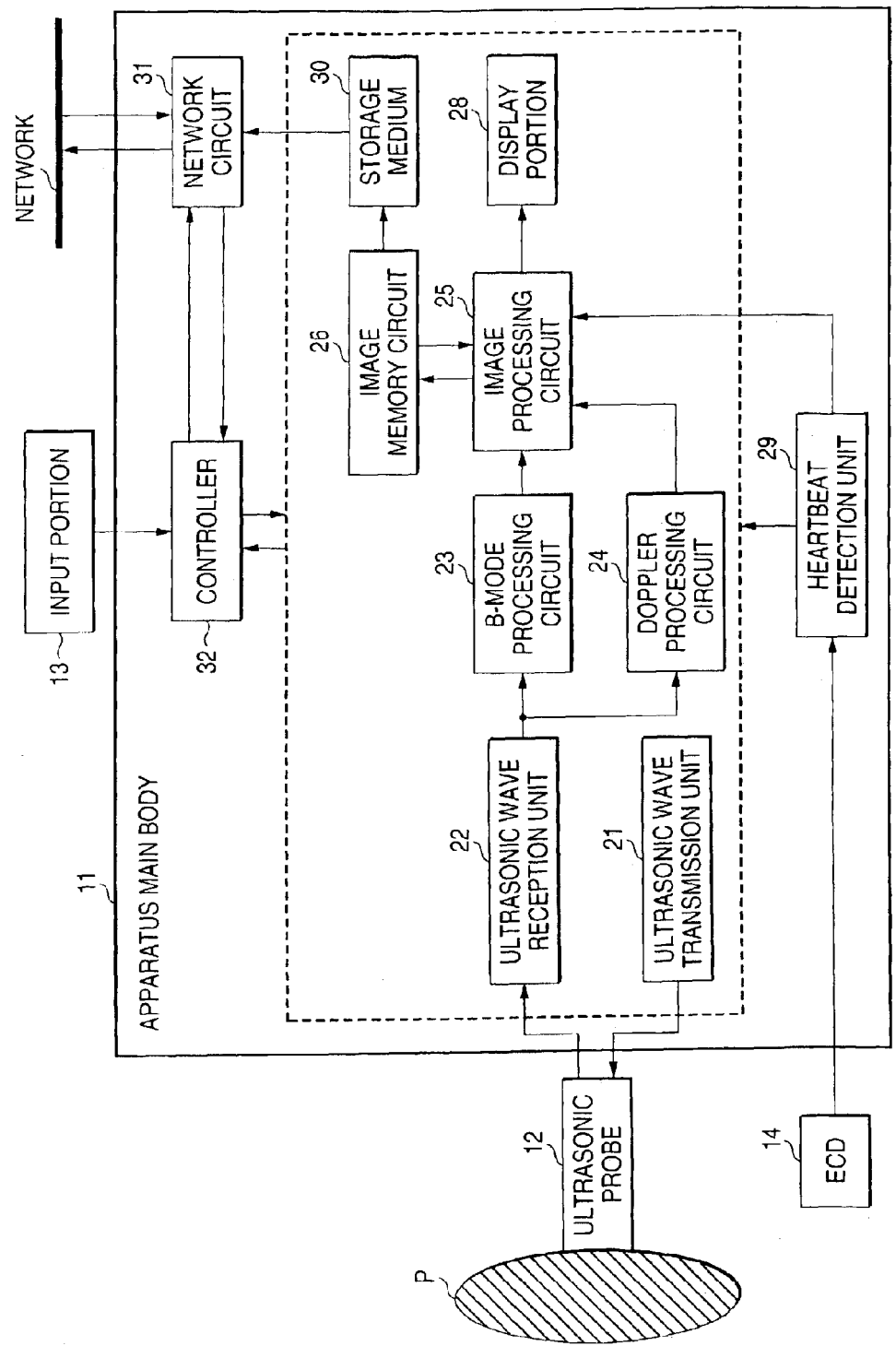
FIG. 1 is a view schematically showing an arrangement of an ultrasonic diagnosis apparatus according to one embodiment.

An embodiment of the invention will now be explained with reference to the drawings. In the following description, components having substantially the same function and arrangement are labeled with the same reference numerals, and the explanation is repeated only when necessary.

A schematic arrangement of an ultrasonic diagnosis apparatus according to this embodiment will be explained first.

FIG. 1 is a view schematically showing an arrangement of an ultrasonic diagnosis apparatus 10 according to this embodiment.

As shown in FIG. 1, the ultrasonic diagnosis apparatus 10 includes an ultrasonic probe 12 responsible for transmission/reception of an ultrasonic signal to/from a subject to be diagnosed, an apparatus main body 11 for driving the ultrasonic probe and processing a reception signal of the ultrasonic probe, an input portion 13 connected to the apparatus main body and allowing the operator to input command information into the apparatus main body, and an ECG 14 for measuring an electrocardiac waveform. The input portion 13 includes buttons, a keyboard, a trackball, etc., which enable control of the diagnosis apparatus and various image-quality condition settings.

The apparatus main body 11 includes an ultrasonic wave transmission unit 21, an ultrasonic wave reception unit 22, a B-mode processing circuit 23, a Doppler processing circuit 24, an image processing circuit 25, an image memory circuit 26, a display portion 28, a heartbeat detection unit 29, a storage medium 30, a network circuit 31, and a controller 32.

The ultrasonic wave transmission unit 21 is composed of a trigger generator, a delay circuit, and a pulsar circuit (all not shown), and it generates a focused ultrasonic pulse by generating a pulsed ultrasonic wave and sending the same to the piezoelectric transducers of the probe 12. The transmission unit 21 is furnished with a switching function of enabling an instantaneous change of a transmission frequency, a transmission driving voltage, etc. at a command from the controller 32. In particular, as to the transmission driving voltage, an instantaneous change is achieved either by having a transmission circuit of a linear amplifier type capable of switching its value instantaneously, or by electrically switching a plurality of power supply units.

Also, the ultrasonic wave transmission unit 21 performs an intermittent transmission of an ultrasonic wave according to a sequence described below (see FIG. 4) under the control of the controller 32. The intermittent transmission referred to herein means, for example, in the case of the contrast medium echo imaging method, a transmission method of periodically repeating an operation such that a transmission of an ultrasonic wave is suspended (for example, for four seconds) and then the transmission of an ultrasonic wave is resumed. According to the intermittent transmission, it is possible to acquire a contrast medium echo signal corresponding to blood flown in during an intermittence time. For example, U.S. Pat. No. 6,149,597 discloses a method of acquiring a time-sequential change of the dynamics of a blood flow by changing a time interval between suspensions.

The ultrasonic wave reception unit 22 receives an echo signal outputted from each transducer of the probe 12, the echo signal having been scattered by tissue within the subject to be diagnosed. The echo signal is amplified by a preamplifier for each channel in the ultrasonic wave reception unit 22, and is given with a delay time needed to determine the reception directivity after analog-to-digital conversion from the reception delay circuit, after which it is added up in an adder. This adding processing is performed to enhance a reflection component from a direction corresponding to the reception directivity of a reflection wave, and a comprehensive ultrasonic beam for transmission and reception can be formed with the transmission directivity and the reception directivity acquired through this processing.

The B-mode processing circuit 23 applies echo signal logarithmic amplification, envelope detection processing, etc. to the echo signal inputted from the ultrasonic wave reception unit 22, and thereby generates data indicating the signal intensity in brightness of luminance.

The Doppler processing circuit 24 performs frequency analysis of speed information from the echo signal, and sends the analysis result to the image processing circuit 25.

The image processing circuit 25 converts an array of scanning line signals of ultrasonic scan into an array of scanning line signals of a typical video format represented by a TV. The image processing circuit 25 synthesizes the converted signal with character information and scales of various setting parameters, and outputs the result to the display portion 28 as a video signal. A tomographic image representing the shape of the tissue within the subject to be diagnosed is thus displayed.

The image processing circuit 25 also generates a TIC (Time Intensity Curve) based on plural pieces of ultrasonic image information thus acquired. The TIC is a graph indicating a time-sequential change of intensity when the history of enhancement of the echo signal after the introduction of a contrast medium is followed in the region of interest, and is used for quantitative analysis in evaluating the dynamics of a blood flow.

The image memory circuit 26 is composed of a storage memory for storing image data. The information stored in the image memory circuit 26 can be, for example, read out after the diagnosis; moreover, a motion picture can be played back using information of more than one frame.

The heartbeat detection unit 29 converts living body signal information, such as an electrocardiogram acquired in the ECG 14, into a digital signal. The digital signal related to the living body signal information is synthesized with a diagnosis image in the image processing circuit 25, and is then displayed on the display portion 28 or recorded in the memory provided to the image memory circuit 26. When the living body signal information is needed for analysis of a technical flow described below, it is saved in the storage medium 30 or transferred to the outside via the network circuit.

The storage medium 30 stores a diagnosis analysis program described below. Also, it is used to save an image in the image memory circuit 26. The data in the storage medium 30 can be also transferred to an outside peripheral apparatus via the network circuit 31.

The controller 32 is furnished with a function of operating as an information processing apparatus (computer), and it is control means for controlling operations of the ultrasonic diagnosis apparatus main body 11. In particular, the controller 32 changes the transmission conditions, such as the frequency and the driving voltage of the transmission unit, from time to time, and appends the information of the transmission conditions to a diagnosis image acquired under the above conditions, which is then appended to image information or stored in the storage medium. The controller 32 is also furnished with a programming function so as to perform a transmission sequence, which is characteristic of the invention.

Prior to an explanation of operations of the ultrasonic diagnosis apparatus of the invention, the theory underlying as the premise will be discussed.

Firstly, general properties of micro-bubbles used as a contrast medium will be discussed. The micro-bubbles (hereinafter, referred to simply as bubbles) can be destroyed with a mechanical function of an ultrasonic sound pressure. Theoretically, the threshold needs to be a function of a frequency or a sound pressure (for example, Holland AK, Apfel RE, "An improved theory for the prediction of micro-cavitation thresholds", IEEE Trans Ultrason Ferroelec Freq Contr 1989; 36, No. 2, 204–208).

Figure 2:
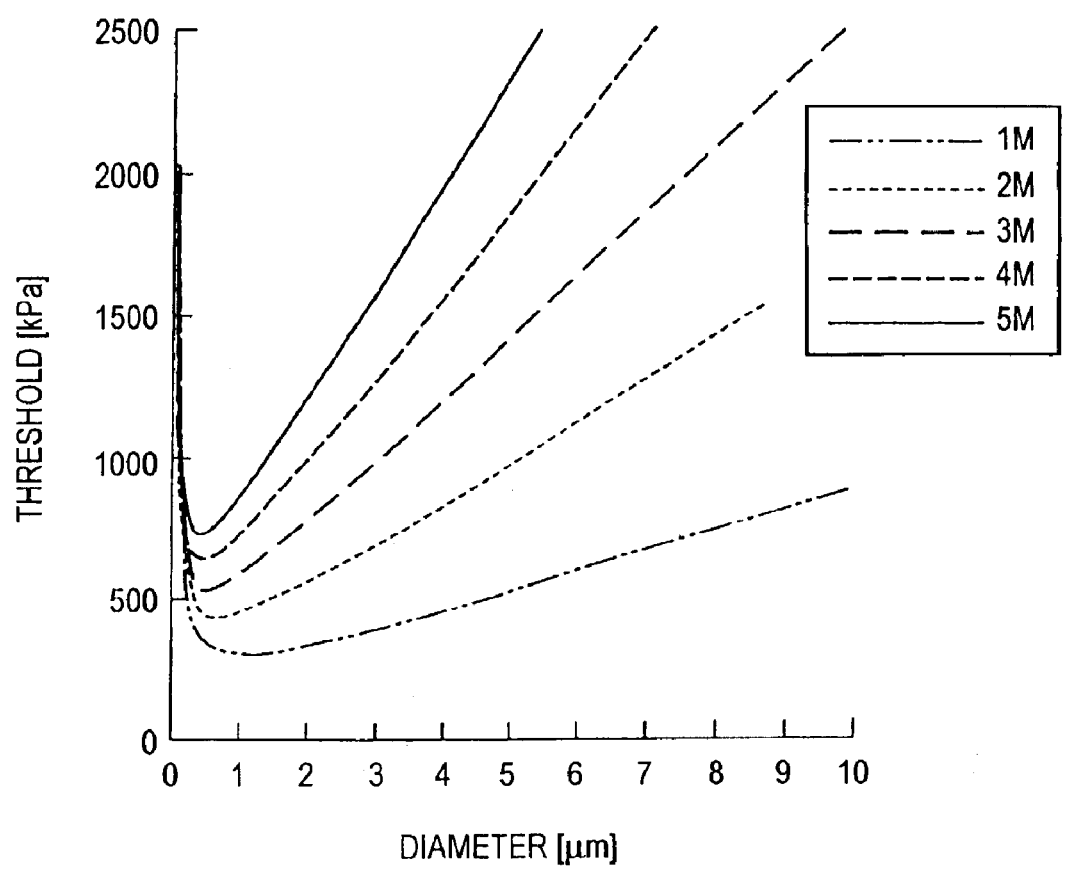
FIG. 2 is a graph showing a theoretical relation between the size of bubbles and a suction pressure needed for destruction.

FIG. 2 is a graph showing a relation between an initial diameter of bubbles and the threshold of a sound pressure needed to destroy the bubbles of each initial diameter, calculated from the theoretical equation in the article supra. It is understood from the graph that the higher the irradiation sound pressure becomes, the more readily the bubbles collapse, and the lower the irradiation frequency becomes, the more readily the bubbles collapse. In addition, the level of a sound pressure needed for destruction also varies with the sizes of bubbles, and it is understood that the irradiation sound pressure needs to be raised in order to destroy larger bubbles.

The dynamics of bubbles of a contrast medium within a living body will now be described. The average size, the number of bubbles per unit volume, etc. of the commercially available contrast media vary depending on the kinds of the product. A typical diameter of the bubbles is approximately 2 to 4 $\mu$m, which is a size slightly smaller than the red blood cells. Hence, the bubbles of a contrast medium can readily pass through the blood capillaries.

However, not all the bubbles have the diameter of 2 to 4 $\mu$m because of the nature of the bubbles, and part of the bubbles has a diameter outside of the above-specified range. The bubbles having a size of other than 2 to 4 $\mu$m, for example, the bubbles having a size of approximately 1 $\mu$m function as extremely small sources of echoes as long as they maintain that size. On the other hand, the bubbles having a size of approximately 1 $\mu$m is quite vulnerable to destruction with respect to a sound pressure as shown in FIG. 2, and in particular, they have natural disposition that they expand with a suction pressure and become large sources of echoes. Also, for example, the bubbles of a size of approximately 6 $\mu$m account for a small ratio; however, because a reflection echo per count is originally large, they function as large sources of echoes.

Hence, the bubbles of a size of approximately 6 $\mu$m are thought to possibly behave in the same manner as the red blood cells, and circulate throughout the body without leaking from the blood capillary walls. On the other hand, the bubbles of a size of approximately 1 $\mu$m are thought to possibly leak from the blood capillary walls and seep out to cavities between the leaking cell membranes. In particular, the latter is attested by the fact described in the following.

There are a number of interstices called Disse's cavities of a size of approximately 1 $\mu$m in the sinusoid of the liver. Nutrition and substances at the level of oxygen molecules readily flow into the Disse's cavities. Thus, assume that the bubbles of a size of approximately 1 $\mu$m seep out from the blood capillary walls to the cavities between the leaking cell membranes as described above, then it is predicted that the bubbles of a size of approximately 1 $\mu$m flow into the Disse's cavities as well. In fact, it is known that when the ultrasonic scan is suspended after the introduction of a contrast medium, and irradiation is resumed approximately five minutes later, echoes equal to or larger than those from the blood flow in the blood capillaries are observed in the liver. This fact implies that the bubbles are also flown into a circulation system smaller than the red blood cells.

From the content above, the followings are inferred as to an ultrasonic diagnosis. That is, for example, in a state where the region of interest is fully filled with a contrast medium, it is thought that a group of bubbles having a broad size distribution including a lager size are present in a blood flow circulation system at the level of the red blood cells, whereas a group of bubbles whose sizes are limited to, for example, 1 $\mu$m or less, are present in a blood flow (blood plasma) circulation system smaller than the red blood cells. It is inferred that this characteristic applies to typical abdominal system, in particular, the liver, the kidney, the spleen, etc. As another example, phagocytes called Kupffer cells are present within the liver, which possibly phagocytize the bubbles. It is also thought that the bubbles taken into these cells are limited to those of relative small sizes.

Figure 3A:
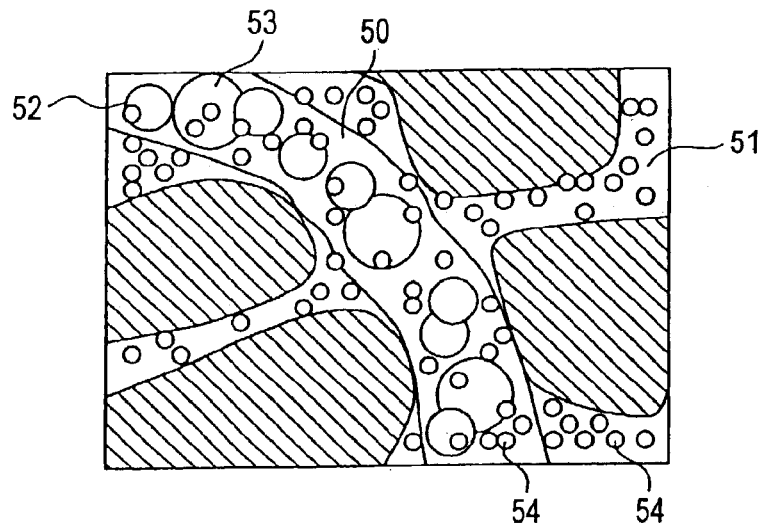
FIG. 3A, FIG. 3B, and FIG. 3C are views conceptually showing microscopic regions where bubbles of different sizes are present.

FIG. 3A is a diagrammatic view used to explain that the bubbles are allowed to flow into different circulation systems depending on their sizes.

As shown in FIG. 3A, bubbles 52 and 53 having a size of approximately 2 to 4 $\mu$m and bubbles 54 having a size of approximately 1 $\mu$m flow into a circulation system 50 (for example, a blood vessel) of the level of the red blood cells, and for example, they circulate with the red blood cells. Also, the bubbles 52 and 53 cannot pass through the blood vessel wall in a circulation system 51 in which the blood plasma or the like circulates, and the circulation system 51 is therefore filled with bubbles 54 of a size of approximately 1 $\mu$m.

The important point of the invention is that the invention focused on that the dynamics of bubbles of a contrast medium within a living body differ depending on their sizes, so that first living body information based on bubbles of a contrast medium of a size comparable to the red blood cells and second living body information based on bubbles of the contrast medium smaller than the red blood cells (for example, bubbles of a size of 1 $\mu$m or less) are imaged or quantified independently. In order to acquire the first living body information and the second living body information adequately, the ultrasonic diagnosis apparatus of the embodiment controls the timings at which the bubbles disappear according to their sizes by performing ultrasonic wave transmissions while changing the transmission conditions described below.

Figure 3B:
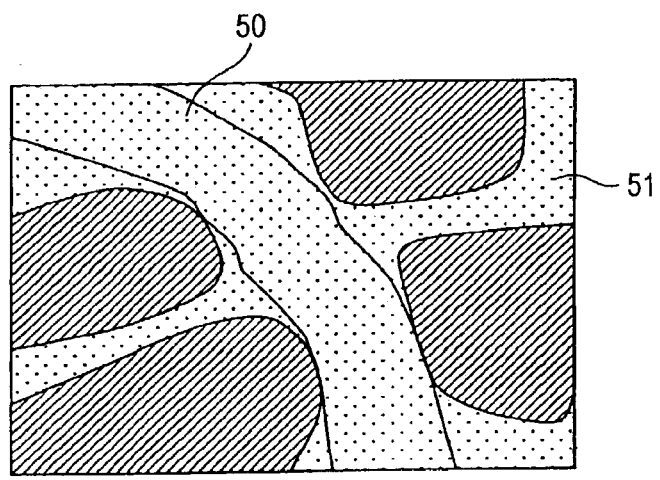
Figure 3C:
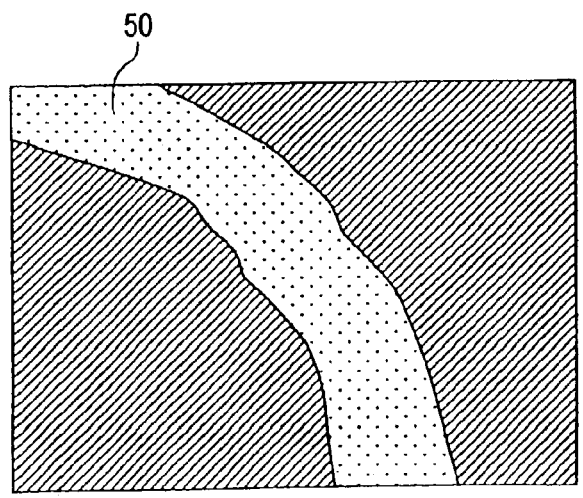

FIG. 3B and FIG. 3(c) are diagrammatic views used to explain the principle to acquire the first living body information and the second living body information.

When ultrasonic irradiation is performed initially at a sound pressure of approximately 500 k Pascal within the region of interest (for example, within the region shown in FIG. 3A) filled with the bubbles, then it is possible to chiefly destroy the bubbles of a size of approximately 1 $\mu$m, which makes it possible to acquire large sources of echoes (echoes as flash echoes). As a result, it is possible to acquire the ecological information from a total region (the region indicated by dots in FIG. 3B) of the circulation system 50 and the circulation system 51 where the bubbles of a size of approximately 1 μm were present. In addition, although it is not clear, because the ecological information is also based on an echo signal from a circulation system at or lower the level of the red blood cells, the ecological information has a possibility of providing new diagnosis information, such as the size of interstices, the function of uptake cells, and the metabolic function.

Subsequently, when irradiation is performed at a sound pressure level of 1000 k Pascal, for example, of all the remaining bubbles that were not destroyed in the last irradiation, it is possible to destroy chiefly the bubbles that are relatively vulnerable to destruction (including the bubbles 52 and 53 of a size of 2 to 4 μm in FIG. 3A), which makes it possible to acquire large sources of echoes (echoes as flash echoes). Consequently, it is possible to acquire the ecological information from the circulation system 50 (the region indicated by dots in FIG. 3C) at the level of the red blood cells where the bubbles 52 and 53 were chiefly present. This ecological information reflects the dynamics of the red blood cells, and therefore becomes useful information for a general diagnosis or quantification of a blood flow.

An operation achieved by the ultrasonic diagnosis apparatus 10 in an ultrasonic diagnosis through the contrast echo imaging method will now be explained chiefly in terms of an ultrasonic wave transmission to a subject to be diagnosed.

Figure 4:
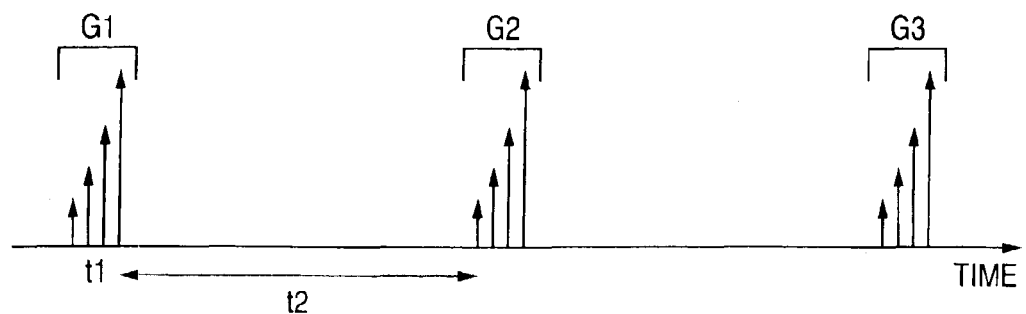
FIG. 4 is a view used to explain one example of a sequence related to a diagnosis made by the ultrasonic diagnosis apparatus 10.

FIG. 4 is a view used to explain one example of an ultrasonic wave transmission sequence for an abdominal diagnosis performed by the ultrasonic diagnosis apparatus 10.

Referring to FIG. 4, the abscissa is used as an elapse of time. The ordinate is used as the strength of a mechanical function resulted from a transmission and applied to the bubbles, and the higher the value of the ordinate becomes, the lower the transmission frequency becomes (alternatively, the higher the transmission driving sound pressure becomes, or a combination of the foregoing). According to this sequence, the mechanical function is controlled step by step according to the sizes of the bubbles to be destroyed.

Also, each group of arrows in the drawing (G1, G2, G3, and so forth in the drawing) represents the ultrasonic scan of one frame, and the lengths of the respective arrows reflect the strength of the mechanical function of a transmission sound pressure of the frame in question (that is, the longer the arrow becomes, the higher the strength becomes). For example, the group G1 of the transmission frame indicates so-called four consecutive transmissions in an ultrasonic diagnosis, and an interval t1 is a frame interval. The four ultrasonic wave transmissions in each group (for example, in the group G1) are not necessarily performed at regular intervals.

Also, an inverse number 1/t1 corresponds to a so-called frame rate. A time interval t2 indicates a so-called intermittent transmission interval, which is a relatively long time interval in comparison with frame intervals for a normal diagnosis. To be more specific, it is preferable that t2 is approximately 3 to 5 seconds, which is an interval needed for the region of interest to be filled with the bubbles, or longer.

The characteristic point of the ultrasonic wave transmission sequence shown in FIG. 4 is that transmissions are performed through the intermittent transmissions in such a manner that the mechanical function increases gradually after the region of interest of the organs is filled with the bubbles, so that two or more frames are acquired. By increasing the mechanical function step by step in this manner, it is possible to give rise to destruction of bubbles of a contrast medium smaller than the red blood cells (for example, bubbles of a size of 1 μm or less) and destruction of bubbles of the contrast medium of a size comparable to the red blood cells at different timings. This enables isolation of the living body information from the blood flow circulation system for circulating the red blood cells and the living body information from the blood flow (plasma) circulation system smaller than the red blood cells.

The ultrasonic wave transmissions by the ultrasonic diagnosis apparatus are aimed at destroying two kinds of bubbles (bubbles of a contrast medium smaller than the red blood cells and bubbles of the contrast medium of a size comparable to the red blood cells as described above) at different timings. Hence, it is sufficient to perform at least two ultrasonic wave transmissions in the ultrasonic scan of one frame. Nevertheless, in the case shown in FIG. 4, four ultrasonic wave transmissions are performed in one frame. This is done so to enable more accurate judgment as to in which irradiation out of four ultrasonic irradiations the destruction of bubbles of a contrast medium of a size comparable to the red blood cells took place. By performing a greater number of ultrasonic transmissions in the ultrasonic scan of one frame in this manner, it is possible to distinguish, more accurately, the living body information from the blood flow circulation system for circulating the red blood cells from the living body information from the blood flow (plasma) circulation system smaller than the red blood cells.

Also, the sequence is repeated in G2, G3 and so forth. This is done so to generate TIC's composed of the respective kinds of information: the living body information from the blood flow circulation system for circulating the red blood cells, and the living body information from the blood flow (plasma) circulation system smaller than the red blood cells, in addition to acquisition of ultrasonic images.

A diagnosis protocol adopting the transmission sequence of FIG. 4 will now be explained with reference to FIG. 5.

Figure 5:
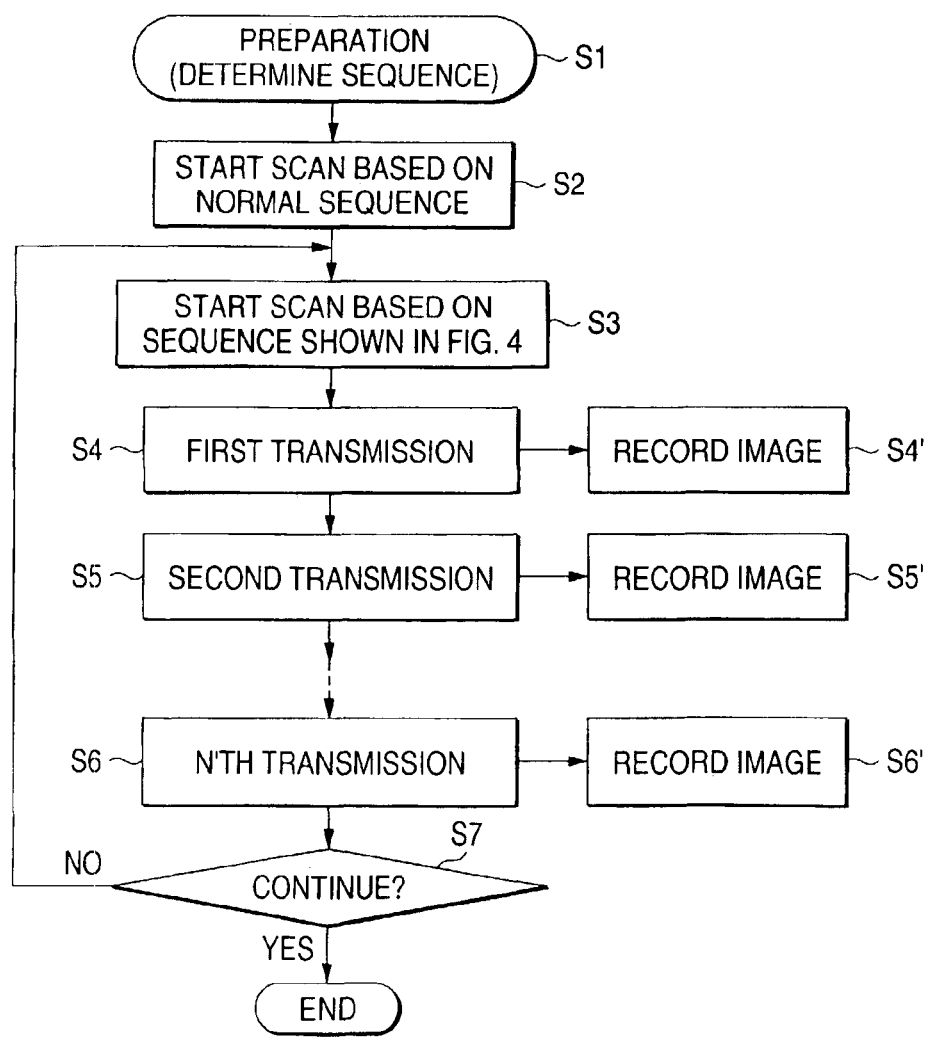
FIG. 5 is a flowchart showing a scan protocol performed by the ultrasonic diagnosis apparatus 10.

FIG. 5 is a flowchart used to explain the diagnosis protocol performed by the ultrasonic diagnosis apparatus 10.

Referring to FIG. 5, the operator initially determines the sequence shown in FIG. 4 uniquely by programming the respective parameters as preparation prior to a screening (Step S1).

To be more concrete, the operator inputs values for the number N of transmission frames (that is, the number of groups G1, G2, and so forth of arrows of FIG. 4), the driving frequency and the driving sound pressure for each transmission (that is, the transmission conditions), the frame interval t1, the intermittent transmission interval t2, etc. Herein, the number N of the transmission frames=6, and the ultrasonic wave transmissions of one frame are performed while increasing the mechanical function in four steps as shown in FIG. 4.

It may be arranged in such a manner that the operator can determine the sequence by choosing a desired program interactively from a plurality of pre-installed programs.

Then, the operator starts the scan of the subject to be diagnosed based on a normal sequence (Step S2).

The scan in this step is for observation in the B-mode, the Doppler mode, etc. generally performed before the introduction of a contrast medium. Hence, in this step, the scan is performed based on not the sequence shown in FIG. 4 but on a normal sequence.

Then, a contrast medium is introduced, and the ultrasonic sound transmissions or the like based on the sequence shown in FIG. 4 are started (Step S3).

The start manipulation is performed with the pressing of a button provided to the input portion 13.

Subsequently, the scan is performed automatically based on the transmission sequence shown in FIG. 4 (Step S4 through Step S6). More specifically, the ultrasonic wave transmissions of one frame corresponding to G1 of FIG. 4 are performed first, and echo signals corresponding to the respective ultrasonic waves are received. The respective echo signals thus received are subjected to predetermined processing and recorded into the image memory or the storage medium as image information, so that images together with the information of the transmission conditions in each step of the mechanical function are recorded.

Subsequently, the ultrasonic wave transmissions of six transmission frames are repeated with the set intermittent interval t2 (t2 can be set to vary each time) (Step S7, etc.). In Step S7, upon judgment that a total number of the transmission frames has reached six, the ultrasonic diagnosis apparatus 10 terminates the transmission sequence shown in FIG. 4 (Step S8).

The termination of this sequence can be performed when the operator presses the end button in the input portion. However, it may be arranged in such a manner that, for example, the number of repetitions is recorded in a pre-installed program and the sequence is terminated automatically when the predetermined number of transmissions are performed.

A group of images recorded according to the above procedure are read out later, and displayed on the display portion 28. In this instance, the transmission conditions corresponding to the image being displayed are displayed concurrently on the display portion 28. Also, it is possible to play back a group of recorded frames consecutively, frame-by-frame, inversely, side-by-side, etc.

Further, the ultrasonic diagnosis apparatus is furnished with a function of regrouping a plurality of ultrasonic images acquired based on the sequence shown in FIG. 4, so that they are displayed in groups having the same transmission conditions. The regrouping of the images is achieved based on the transmission conditions and the time information appended to each piece of image data. To be more concrete, the image data appended with the same transmission conditions is extracted, and the extracted image data is further arranged time-sequentially based on the time information.

Figure 6:
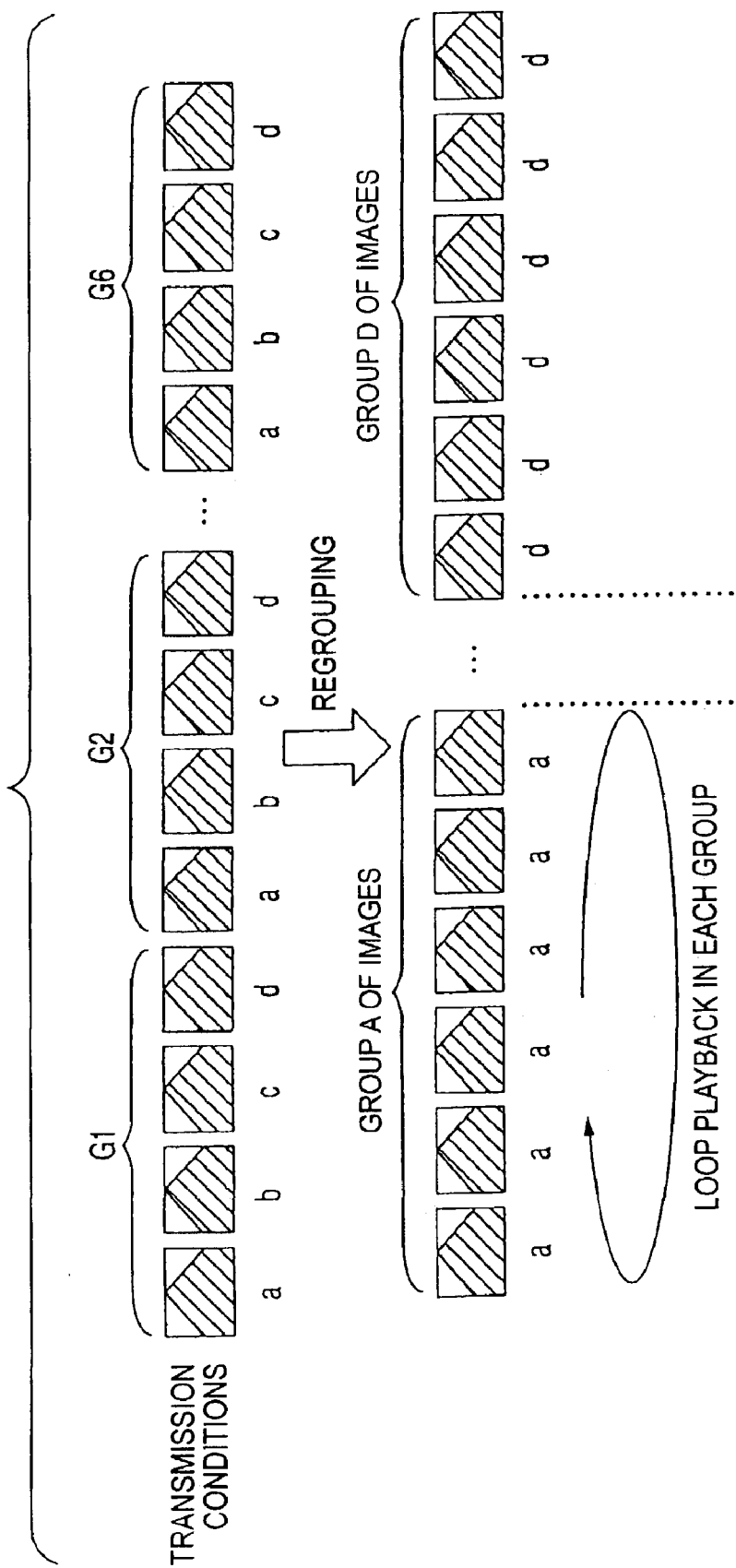
FIG. 6 is a view conceptually showing regrouping processing of recorded images in the embodiment.

FIG. 6 is a view used to explain the image regrouping function.

Respective images "a", "b", "c", and "d" (upper row in the drawing) in each image frame shown in the upper row of FIG. 6 are classified into groups of images based on the transmission conditions as shown in the lower row in the drawing, and are further arranged time-sequentially. Because each group of images regrouped in this manner is composed of images having the same transmission conditions, each group can be said to reflect the living body information based on the bubbles of a contrast medium having substantially the same diameter. In other words, each image group is unified as either ultrasonic images dominated by the living body information from the blood flow circulation system for circulating the red blood cells or ultrasonic images dominated by the living body information from the blood flow (plasma) circulation system smaller than the red blood cells.

It should be noted that the ultrasonic diagnosis apparatus 10 is able to display images in an arbitrary mode, including loop playback of all the images forming all the image groups, loop playback of all images forming one image group, loop playback of more than one image groups, frame-by-frame playback, etc.

Further, the ultrasonic diagnosis apparatus is furnished with a function of specifying an adequate local region with respect to the acquired image groups (for example, those in the lower row in FIG. 6) and finding the intensity histogram or an average intensity value within the specified region, and a function of computing the time intensity curve (TIC).

Figure 7:
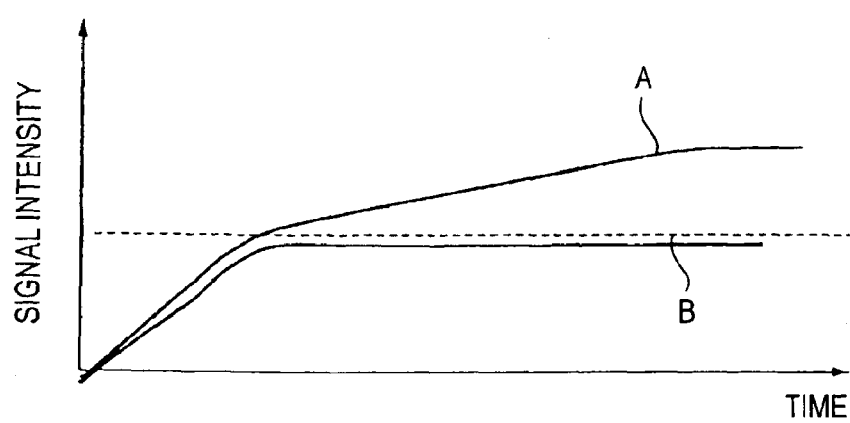
FIG. 7 is a view conceptually showing time intensity curves acquired based on the method of the embodiment.

FIG. 7 shows one example of the respective TIC's acquired from an image group A and an image group B. A curve A indicates the TIC of the image group A and a curve B indicates the TIC of the image group B. In FIG. 7, the ordinate is used as a signal intensity related to the reception ultrasonic waves, and the abscissa is used as an elapsed time (that is, an elapsed time corresponding to the repetitions of the intermittent transmissions).

Referring to FIG. 7, the flow of bubbles indicated by the curve A reflects, besides the flow of the red blood cells, a flow of particles sufficiently smaller than the red blood cells. This is because the curve A is based on images "a" acquired through transmissions at a relatively low sound pressure in each frame. In addition, because the curve A also includes a quite slow flow that leaks out from the blood vessel wall, the intensity continues to rise minutely even after so-called blood flow perfusion reached a saturation state.

On the other hand, in regard to the curve B, a contrast medium in the blood flow reaches saturation in a few seconds. This is because the curve B is based on images "b" acquired through transmissions at a high sound pressure following the transmission at a low sound pressure in each frame, and thereby directly reflects the flow of the red blood cells.

It should be noted that when the aforementioned intermittent interval of scan is extended, the region of interest is filled with the bubbles, and the signal intensity of the TIC rises more abruptly.

Also, the ultrasonic diagnosis apparatus may be furnished with additional functions, so that it can perform image processing, such as addition and subtraction of a plurality of acquired curves.

According to the arrangement described above, because ultrasonic wave transmissions are performed while the mechanical function is increased step by step within one frame, it is possible to induce destructions of bubbles of a contrast medium step by step according to their different sizes. Because the bubbles of a contrast medium are allowed to flow into different regions of the living body depending on their sizes, by generating ultrasonic images using the respective destructions as the sources of echoes, it is possible to provide more diversified information, for example, information reflecting more detailed dynamics of circulating blood and the dynamics of substances smaller than the red blood cells, information of the distribution of predaceous cells, etc. for use in an ultrasonic diagnosis.

It should be appreciated that the invention of this application is not limited to the embodiment described above, and can be modified in various manners in practical stages without departing from the scope of the invention. Also, the respective embodiments can be combined as needed when possible, and combined effects can be achieved in such a case. Further, the embodiment described above includes inventions at various stages, and a variety of inventions can be extracted by adequately combining a plurality of components disclosed above. For example, of all the components shown in the embodiment, even when some components are omitted, the object discussed in the "Problems that the Invention is to Solve" column can be achieved, and in a case where at least one of the advantages described in the "Advantage of the Invention" column is achieved, the arrangement that omits some components can be extracted as an invention.

According to the invention, it is possible to achieve an ultrasonic diagnosis apparatus capable of observing or quantifying bubbles of a contrast medium of a size comparable to the red blood cells and bubbles of the contrast medium of a sufficiently smaller size independently through control of a degree of disappearance of bubbles by changing transmission conditions.

What is claimed is:

1. An ultrasonic diagnosis apparatus, comprising:
    an ultrasonic probe for transmitting/receiving an ultrasonic wave to/from a specific portion within a subject to be diagnosed to whom a contrast medium has been introduced;
    a driving signal generator for generating a driving signal of said ultrasonic probe; and
    a controller for controlling said driving signal generator in such a manner that said ultrasonic probe transmits a first ultrasonic wave used to destroy bubbles of said contrast medium and a second ultrasonic wave used to destroy at least part of bubbles each which substantially has a size larger than a size of each of the bubbles destroyed by said first ultrasonic wave and are flowing in blood in a blood vessel within said subject to be diagnosed.

2. The ultrasonic diagnosis apparatus according to claim 1, wherein said controller controls said driving signal generator in such a manner that said second ultrasonic wave is transmitted at a higher sound pressure than said first ultrasonic wave.

3. The ultrasonic diagnosis apparatus according to claim 1, wherein said controller controls said driving signal generator in such a manner that said second ultrasonic wave is transmitted at a lower frequency than said first ultrasonic wave.

4. The ultrasonic diagnosis apparatus according to claim 1, wherein said controller controls said driving signal generator in such a manner that said first ultrasonic wave or said second ultrasonic wave is transmitted through intermittent transmissions at predetermined time intervals needed to accumulate said contrast medium in said subject to be diagnosed.

5. The ultrasonic diagnosis apparatus according to claim 4, further comprising a display device for displaying, when a plurality of ultrasonic images are acquired by said intermittent transmissions, a plurality of ultrasonic images based on said first ultrasonic wave concurrently or a plurality of ultrasonic images based on said second ultrasonic wave concurrently.

6. The ultrasonic diagnosis apparatus according to claim 5, wherein said display device arranges said plurality of ultrasonic images to be displayed concurrently time-sequentially and then displays said plurality of ultrasonic images.

7. The ultrasonic diagnosis apparatus according to claim 1, wherein said first ultrasonic wave is at a sound pressure at which said contrast medium present in blood in the blood vessel and tissue fluid and lymph outside the blood vessel within said subject to be diagnosed is destroyed.

8. The ultrasonic diagnosis apparatus according to claim 1, wherein said driving signal generator is controlled in such a manner that said first ultrasonic wave is transmitted under a transmission condition under which bubbles of said contrast medium of a small diameter are destroyed but bubbles of said contrast medium of a large diameter are hardly destroyed, and said second ultrasonic wave is transmitted under a transmission condition under which bubbles of said contrast medium of a small diameter and a large diameter are destroyed.

9. The ultrasonic diagnosis apparatus according to claim 1, further comprising:
    a image processing unit configured to generate a first image based on the first ultrasonic wave and a second image based on the second ultrasonic wave; and
    display device which displays the first image and the second image.

10. A method of controlling an ultrasonic diagnosis apparatus for controlling a driving signal generator in such a manner that an ultrasonic probe, which transmits/receives an ultrasonic wave to/from a specific portion within a subject to be diagnosed to whom a contrast medium has been introduced, transmits a first ultrasonic wave used to destroy bubbles of said contrast medium and a second ultrasonic wave used to destroy at least part of bubbles each of which substantially has a size larger than a size of each of the bubbles destroyed by said first ultrasonic wave and are flowing in blood in a blood vessel within said subject to be diagnosed.

11. The method of controlling an ultrasonic diagnosis apparatus according to claim 10, wherein said second ultrasonic wave has a higher sound pressure than said first ultrasonic wave.

12. The method of controlling an ultrasonic diagnosis apparatus according to claim 10, wherein said second ultrasonic wave has a lower frequency than said first ultrasonic wave.

13. The method of controlling an ultrasonic diagnosis apparatus according to claim 10, wherein said driving signal generator is controlled in such a manner that said first ultrasonic wave or said second ultrasonic wave is transmitted through intermittent transmissions at predetermined time intervals needed to accumulate said contrast medium in said subject to be diagnosed.

14. The method of controlling an ultrasonic diagnosis apparatus according to claim 13, wherein, when a plurality of ultrasonic images are acquired by said intermittent transmissions, a display is further presented, in which a plurality of ultrasonic images based on said first ultrasonic wave are displayed concurrently or a plurality of ultrasonic images based on said second ultrasonic wave are displayed concurrently.

15. The method of controlling an ultrasonic diagnosis apparatus according to claim 14, wherein said display is a display in which said plurality of ultrasonic images to be displayed concurrently are arranged time-sequentially.

16. The method of controlling an ultrasonic diagnosis apparatus according to claim 10, wherein said first ultrasonic wave is at a sound pressure at which said contrast medium present in blood in the blood vessel and tissue fluid and lymph outside the blood vessel within said subject to be diagnosed is destroyed.

17. The method of controlling an ultrasonic diagnosis apparatus according to claim 10, wherein said driving signal generator is controlled in such a manner that said first ultrasonic wave is transmitted under a transmission condition under which bubbles of said contrast medium of a small diameter are destroyed but bubbles of said contrast medium of a large diameter are hardly destroyed, and said second ultrasonic wave is transmitted under a transmission condition under which bubbles of said contrast medium of a small diameter and a large diameter are destroyed.

18. The method of controlling an ultrasonic diagnosis apparatus according to claim 10, further comprising:
    generating a first image based on the first ultrasonic wave and a second image based on the second ultrasonic wave; and
    displaying the first image and the second image.

* * * * *